US00PP33134P2

(12) United States Plant Patent
de Groot

(10) Patent No.: US PP33,134 P2
(45) Date of Patent: Jun. 8, 2021

(54) ***ROSA* PLANT NAMED 'RUIRI0109A'**

(50) Latin Name: *Rosa hybrida*
Varietal Denomination: RUIRI0109A

(71) Applicant: De Ruiter Intellectual Property B.V., Amstelveen (NL)

(72) Inventor: Hendrikus Cornelis Adrianus de Groot, Amstelveen (NL)

(73) Assignee: De Ruiter Intellectual Property B.V.

( * ) Notice: Subject to any disclaimer, the term of this patent is extended or adjusted under 35 U.S.C. 154(b) by 0 days.

(21) Appl. No.: 16/987,186

(22) Filed: Aug. 6, 2020

(51) Int. Cl.
*A01H 5/02* (2018.01)
*A01H 6/74* (2018.01)

(52) U.S. Cl.
USPC ..... Plt./104
CPC ..... *A01H 6/749* (2018.05)

(58) Field of Classification Search
USPC ..... Plt./104
CPC ..... A01H 6/749
See application file for complete search history.

*Primary Examiner* — Anne Marie Grunberg
(74) *Attorney, Agent, or Firm* — Cassandra Bright

(57) ABSTRACT

A new and distinct cultivar of hybrid *Rosa* plant named, 'RUIRI0109A' is disclosed, characterized by pure yellow flowers on highly floriferous plants. Foliage is very glossy. The new variety is a multiflora landscape type garden rose.

2 Drawing Sheets

Figure 1:
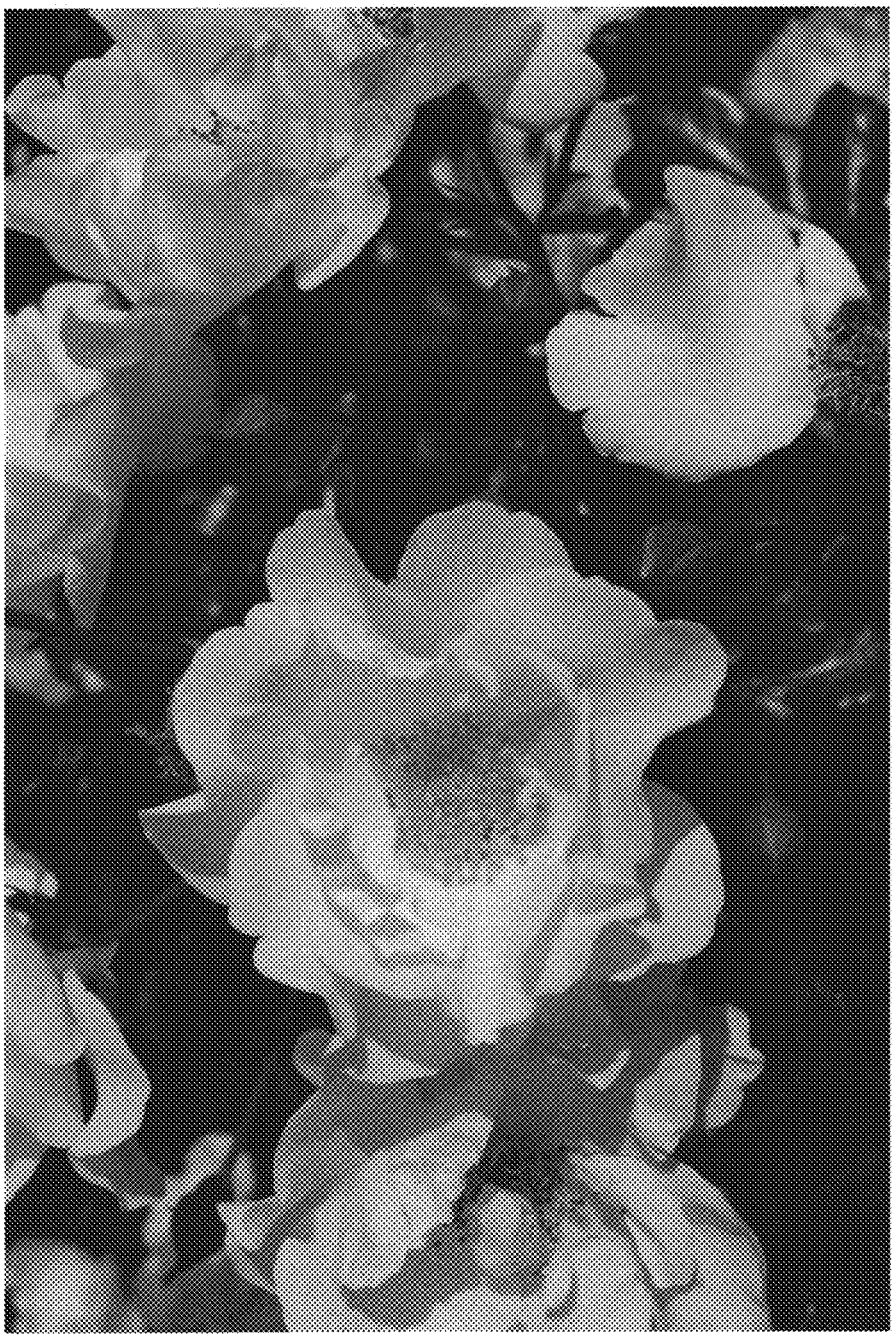

Latin name of the genus and species: *Rosa hybrida.*
Variety denomination: 'RUIRI0109A'.

BACKGROUND OF THE INVENTION

The new *Rosa* cultivar is a product of a planned breeding program conducted by the inventor. The cross resulting in this new variety was made in Spring of 2010 at a nursery in Boskoop, The Netherlands.

The seed parent is the unpatented variety *Rosa* 'BOKRARUIROL'. The pollen parent is the unpatented variety *Rosa* 'NOA75800'. The new variety was selected in Autumn of 2012 by the inventor at the same nursery in Boskoop, The Netherlands. The inventor continued observing characteristics of the new variety for several years, in the controlled conditions of the research nursery.

Asexual reproduction of the new cultivar was performed by vegetative softwood cuttings. This was first performed at a greenhouse in Amstelveen, The Netherlands, in May 2013, and has shown that the unique features of this cultivar are stable and reproduced true to type in successive generations.

SUMMARY OF THE INVENTION

The cultivar 'RUIRI0109A' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RUIRI0109A' These characteristics in combination distinguish 'RUIRI0109A' as a new and distinct *Rosa* cultivar:

1. Yellow flowers.
2. Brown thorns.
3. Glossy leaves.
4. Ovate-shaped leaflet blade.
5. Acute blade apex.
4. Suitability for landscape and groundcover use.

5. Flowering continuously from June until October in the Netherlands.

PARENTAL COMPARISON

Plants of the new cultivar 'RUIRI0109A' are similar to plants of the seed parent, in most horticultural characteristics, however, plants of the new cultivar 'RUIRI0109A' differ in the following:

1. Thorns of the new variety are brown, thorns of the seed parent are red.
2. Foliage of the new variety is glossier than foliage of the seed parent.

Plants of the new cultivar 'RUIRI0109A' are similar to plants of the pollen parent in most horticultural characteristics, however, plants of the new cultivar 'RUIRI0109A' differs in the following;

1. Flower color of the new variety is yellow; flower color of the pollen parent is orange.
2. Foliage of the new variety is glossier than foliage of the pollen parent.

COMMERCIAL COMPARISON

Plants of the new cultivar 'RUIRI0109A' can be compared to the commercial variety *Rosa* 'NOALESA' U.S. Plant Pat. No. 13,869. These varieties are similar in most horticultural characteristics, however 'RUIRI0109A' differs in the following:

1. The new variety has bronze hue on the leaf coloration not see in this comparator.
2. Flower stems of the new variety are stronger than those of this comparator.

Plants of the new cultivar 'RUIRI0109A' can be compared to the unpatented commercial variety *Rosa* 'DELDOG', unpatented. These varieties are similar in most horticultural characteristics, however 'RUIRI0109A' differs in the following:

1. Flower color of the new variety doesn't fade as much as flower color of this comparator.
2. Plants of the new variety grow more compactly than plants of this comparator.

BRIEF DESCRIPTION OF THE PHOTOGRAPHS

The accompanying photograph in FIG. 1 illustrates a close-up view of a typical inflorescence.

Figure 2:
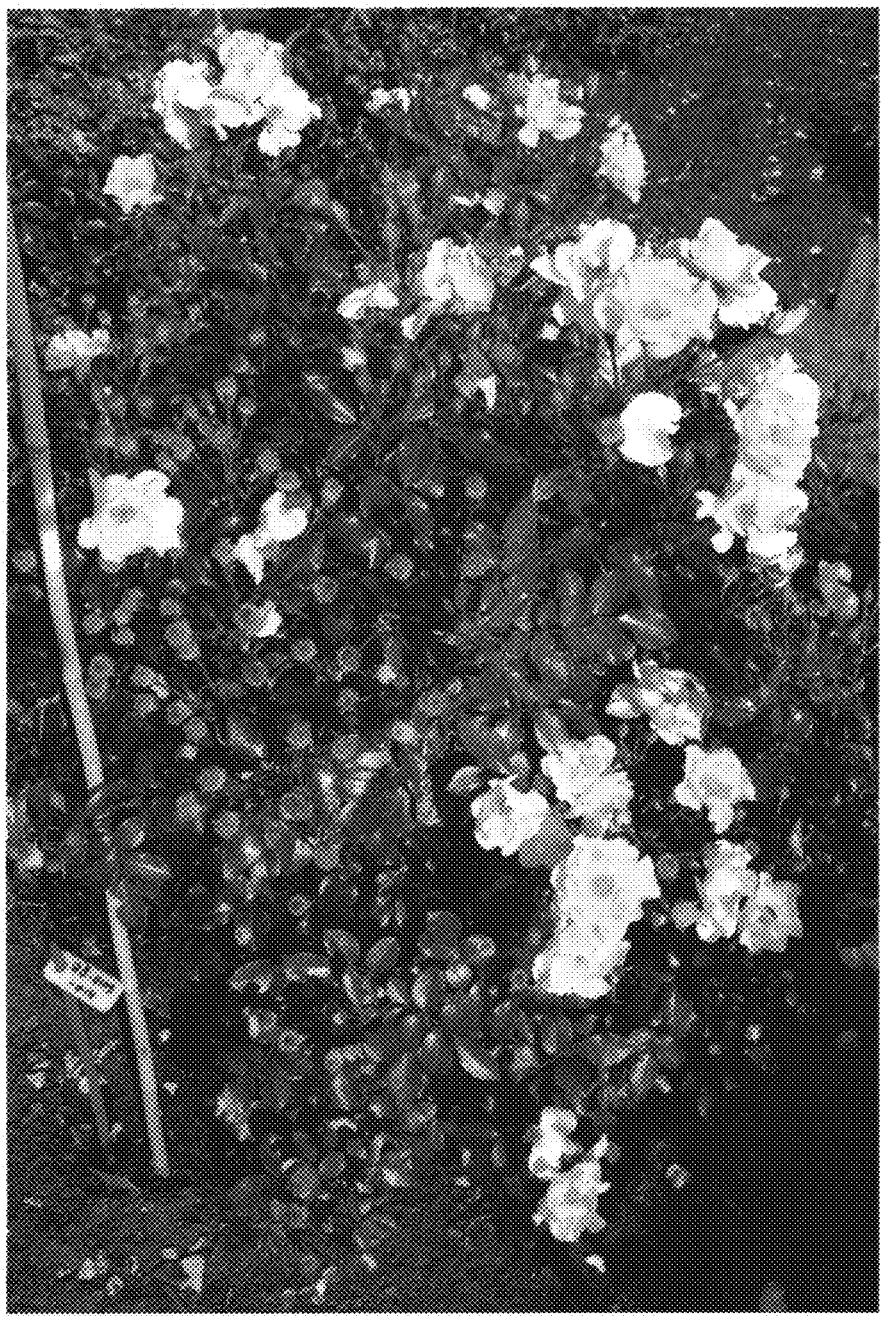

FIG. 2 illustrates in full color typical plants of 'RUIRI0109A' grown in the ground at a nursery in De Kwakel, The Netherlands. Plants in FIG. 2 are approximately 2 years old.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'RUIRI0109A' plants grown outdoors, in De Kwakel, The Netherlands. The growing temperature ranged from approximately 20° C. to 26° C. during the day and from approximately 16° C. to 18° C. during the night. Measurements were taken in August. General light conditions were very bright, normal sunlight. Measurements and numerical values represent averages of typical plant types.

Botanical classification: *Rosa* 'RUIRI0109A'.

Market classification: Landscape/groundcover multiflora.

PROPAGATION

Time to initiate roots: 10 days at approximately 25° C.

Time to produce a rooted cutting: 21 days at approximately 25° C.

Typical method: Vegetative terminal cuttings, does not require grafting.

PLANT

Growth habit: Intermediate.

Age of plant described: 2 years.

In a container or in the ground: Ground.

Height: 50 cm.

Plant spread: 40 cm.

Branching characteristics:

Length of primary lateral branches: Approximately 28 cm.

Diameter of lateral branches: Approximately 8 cm.

Quantity of lateral branches: 3 to 6 main lateral branches.

Branching arrangement: Compound.

Branches-young wood:

*Diameter*.—Approximately 0.4 cm.

*Texture*.—Smooth.

*Approximately density/quantity of thorns*.—Dense.

*Color*.—Near RHS Yellow-Green 146C.

Branches-old wood:

*Diameter*.—Approximately 0.6 cm, after 0.5 years.

*Color*.—Near RHS Yellow-Green 146B.

*Texture*.—Smooth.

*Approximate density/quantity of thorns*.—Few.

*Thorns*.—Color: Near RHS Brown 200C. Height: 0.8 cm. Diameter: 0.8 cm.

FOLIAGE

Leaf:

*Arrangement*.—Imparipinnate.

*Quantity*.—Approximately 6 per main branch.

*Average length*.—Approximately 9 cm.

*Average width*.—Approximately 7 cm.

Leaflet:

*Quantity*.—3, 5, or 7 per leaf.

*Average length*.—Approximately 4.5 cm.

*Average width*.—Approximately 3 cm.

*Shape of blade*.—Ovate.

*Apex*.—Acute.

*Base*.—Obtuse.

*Margin*.—Serrate.

*Texture of top surface*.—Smooth.

*Texture of bottom surface*.—Smooth.

*Appearance of top surface*.—Very glossy.

*Appearance of bottom surface*.—Matte.

*Leaf internode length*.—3-4 cm.

*Color*.—Young foliage upper side: Near RHS Green 137A with an overall hue near Greyed-Orange 172A. Young foliage under side: Near RHS Yellow-Green 147C. Mature foliage upper side: Near RHS Green NN137A. Mature foliage under side: Near RHS Yellow-Green 147B.

*Venation*.—Type: Pinnate. Venation color upper side: Immature near Greyed-Orange 172A, mature near Yellow-Green N144B. Venation color under side: Near RHS Green 137D.

Stipule:

*Length*.—1.6 cm.

*Width*.—0.5 cm.

*Color*.—Near RHS Green 138C.

*Texture*.—Smooth.

Petiole:

*Length*.—1.5 cm.

*Width*.—0.2 cm.

*Color*.—Immature near Greyed-Red 178C, mature near Yellow-Green N144C.

*Texture*.—Pubescent.

Rachis:

*Length*.—1.7 cm.

*Width*.—0.2 cm.

*Color*.—Immature near Greyed-Red 178C, mature near Yellow-Green N144C.

*Texture*.—Pubescent.

FLOWER

Natural flowering season: June-October in Europe.

Begins flowering after how many years/months: 2 months.

Inflorescence type: Multiflora.

Rate of flower opening: Approximately 3 days from bud to fully opened flower.

Flower longevity on plant: 7 days, after fully opened.

Quantity of flowers: 10 flowers per inflorescence.

Inflorescence size:

*Diameter*.—Approximately 13 cm.

*Length*.—Approximately 12 cm.

Flower size:

*Diameter*.—Approximately 6 cm.

*Length*.—Approximately 4 cm.

Peduncle:
*Length.*—4 cm.
*Diameter.*—0.25 cm.
Petals:
*Petal arrangement*.—Rotate, loose.
*Length.*—3 cm.
*Width.*—4 cm.
*Shape.*—Transverse elliptic.
*Margin*.—Undulate.
*Apex*.—Retuse.
*Base*.—Rounded.
*Petal quantity.*—10.
*Texture*.—Smooth.
*Color*.—When opening: Upper surface: Near RHS Yellow 12B. Lower surface: Near RHS Yellow 10B. Fully opened: Upper surface: Near RHS Yellow 9D. Lower surface: Near RHS Yellow 9D.
Bud:
*Shape*.—Oval.
*Length*.—Approximately 1.5 cm.
*Diameter*.—Approximately 1.1 cm.
*Color*.—Near RHS Yellow 13B.
Sepals:
*Length.*—1.7 cm.
*Width.*—0.8 cm.
*Shape*.—Lanceolate.
*Color*.—Interior Surface: Near RHS Green 143C. Exterior Surface: Near RHS Green 143C flushed Greyed-Purple 187A.
*Texture*.—Smooth.
Receptacle:
*Length.*—0.8 cm.
*Width.*—0.7 cm.
*Shape*.—Round.
*Color*.—Near RHS Yellow-Green 144D lightly flushed Greyed-Purple 187A.
Fragrance: None.

REPRODUCTIVE ORGANS

Stamens:
*Quantity*.—Average 60.
*Filament length*.—Average 0.7 cm.
*Filament color*.—RHS Yellow-Orange 14C.
Anthers:
*Length.*—2 mm.
*Shape*.—Oblong.
*Color*.—RHS Yellow-Orange 22A.
*Pollen*.—Color: RHS Yellow-Orange 22A. Quantity: Scant to moderate.
Pistil:
*Number.*—30.
*Length.*—3 mm.
*Style*.—Length: Approximately 0.4 cm. Color: Near RHS Red 44C.
Stigma:
*Shape*.—Orbicular.
*Color*.—Near RHS Greyed-Orange 162A.

OTHER CHARACTERISTICS

Seeds and fruits: Not observed.
Disease/pest resistance: Neither resistance nor susceptibility to typical diseases and pests of landscape roses observed.
Temperature tolerance: USDA zones 4-9.

What is claimed is:

1. A new and distinct hybrid cultivar of *Rosa* multiflora landscape plant named 'RUIRI0109A' as herein illustrated and described.

* * * * *